United States Patent
Kemp et al.

(10) Patent No.: US 8,761,469 B2
(45) Date of Patent: Jun. 24, 2014

(54) ARTIFACT MANAGEMENT IN ROTATIONAL IMAGING

(75) Inventors: Nathaniel J. Kemp, Concord, MA (US); Vladimir Zagrodsky, El Dorado Hills, CA (US)

(73) Assignee: Volcano Corporation, San Diego, CA (US)

( * ) Notice: Subject to any disclaimer, the term of this patent is extended or adjusted under 35 U.S.C. 154(b) by 248 days.

(21) Appl. No.: 12/983,709

(22) Filed: Jan. 3, 2011

(65) Prior Publication Data

US 2012/0170848 A1    Jul. 5, 2012

(51) Int. Cl.
*G06K 9/00* (2006.01)
*G06T 7/00* (2006.01)

(52) U.S. Cl.
CPC .................. *G06T 7/0012* (2013.01)
USPC ........................................ 382/128

(58) Field of Classification Search
USPC .................... 382/275, 132; 600/407
See application file for complete search history.

(56) References Cited

U.S. PATENT DOCUMENTS

| | | | |
|---|---|---|---|
| 5,325,198 A | 6/1994 | Hartley | |
| 6,895,106 B2 * | 5/2005 | Wang et al. | 382/132 |
| 7,245,125 B2 | 7/2007 | Harer | |
| 2002/0034276 A1 * | 3/2002 | Hu et al. | 378/8 |
| 2003/0152259 A1 * | 8/2003 | Belykh et al. | 382/132 |
| 2006/0036167 A1 * | 2/2006 | Shina | 600/433 |
| 2006/0241465 A1 * | 10/2006 | Huennekens et al. | 600/458 |
| 2007/0167710 A1 * | 7/2007 | Unal et al. | 600/407 |
| 2007/0232890 A1 * | 10/2007 | Hirota | 600/407 |
| 2007/0232891 A1 * | 10/2007 | Hirota | 600/407 |
| 2007/0232892 A1 * | 10/2007 | Hirota | 600/407 |
| 2007/0250000 A1 * | 10/2007 | Magnin et al. | 604/103.04 |
| 2008/0177138 A1 * | 7/2008 | Courtney et al. | 600/109 |
| 2008/0177183 A1 * | 7/2008 | Courtney et al. | 600/463 |
| 2008/0292173 A1 | 11/2008 | Hsieh | |
| 2009/0046295 A1 | 2/2009 | Kemp | |

OTHER PUBLICATIONS

International Search Report and Written Opinion in PCT/US11/67339, mailed May 10, 2012, 12 pages.

* cited by examiner

*Primary Examiner* — Hadi Akhavannik
(74) *Attorney, Agent, or Firm* — Thomas C. Meyers; Brown Rudnick LLP (57) ABSTRACT

A method for artifact management in a rotational imaging system is presented. The method includes the steps of acquiring data employing a helical scanning pattern over N revolutions, where N is greater than 1, and detecting at least one artifact in the acquired data of each revolution. The method further includes segmenting the data acquired over N revolutions into N-1 data frames each bounded by at least one of the at least one artifacts.

10 Claims, 8 Drawing Sheets

ARTIFACT MANAGEMENT IN ROTATIONAL IMAGING

CROSS-RELATED APPLICATIONS

Not Applicable.

FIELD OF THE INVENTION

The present invention relates generally to a method for overlapping artifacts in an in vivo imaging system. More particularly, the present invention pertains to a method for overlapping seam line and guidewire shadow artifacts in an in vivo intravascular imaging system having a rotational imaging catheter and one or more guidewires.

BACKGROUND OF THE INVENTION

Rotational intravascular imaging or sensing technologies, for example, optical coherence tomography (OCT), intravascular ultrasound (IVUS), near infrared (NIR) spectroscopy, and others typically employ point-scanning beam patterns in the shape of a helix, which captures information in rotational and longitudinal directions. A three-dimensional space scanned within a single rotational period generates information which is usually projected into a planar (2D) format for display on a video monitor or other display device. However, such a planar format includes a discontinuity in the data because of longitudinal displacement of the beam during rotation. For example, a data discontinuity, or seam line, is generated at 0° and at 360°. Such a seam line is a disadvantageous artifact of the planar format.

In addition to the seam line artifact, information acquired with a catheter which is placed within a vessel alongside a guidewire can contain an artifact arising from the inability of the beam energy (e.g. light or sound) to adequately penetrate the guidewire. Thus, OCT, rotational IVUS, Intravascular Spectroscopy (IS), Photo-Acoustic Tomography (PAT), or any intravascular imaging or sensing method which uses a rotating transducer or probe in parallel with at least one guidewire or some other shadowing element creates an artifact in the information acquired in every rotation. Such an artifact, generally known as a guidewire shadow, has traditionally been considered an unavoidable but tolerable discontinuity or gap in the information acquired.

There have been attempts to minimize the effects of the seam line or guidewire shadow artifacts. For example, minimizing the seam line artifact by keeping the pitch of the helix tight (high rotation to translation ratio) and thus reducing the longitudinal displacement incurred between the first and last rotational position in a single frame is known in the art. However, this approach only minimizes the appearance of the seam line and does nothing to address the guidewire artifact. There is currently no method known to minimize the effects of both the seam line and guidewire artifacts in an intravascular imaging modality.

SUMMARY OF THE INVENTION

The method described herein minimizes the effects of both the seam line and guidewire shadow artifacts by orienting the seam line artifact so that it overlaps the guidewire artifact in an intravascular image. The method reduces two discontinuous image artifacts in a display frame (the seam line and guidewire shadow) into a common rotational position, which results in a single traditionally tolerable gap in the information acquired and improved image appearance for an end user of the image. Another embodiment of the method is that a three dimensional dataset is rotationally registered to keep the guidewire shadow at a common rotational position throughout a longitudinal scan, thus insuring that a longitudinal cross-section or representation of the data along a plane that contains the longitudinal axis of the catheter (known as the ILD projection of a data set) only suffers from the guidewire shadow at a single slice angle. The method is applicable to any rotational imaging in which a periodic image discontinuity is evident.

In one aspect of the present invention, a method for artifact management in a rotational imaging system is presented. The method includes the steps of acquiring data employing a helical scanning pattern over N revolutions, where N is greater than 1, and detecting at least one artifact in the acquired data of each revolution. The method further includes segmenting the data acquired over N revolutions into N-1 data frames each bounded by at least one of the at least one artifacts.

In another aspect of the present invention, a method for artifact management in a rotational imaging system is presented. The method includes the steps of acquiring data employing a helical scanning pattern over N revolutions, where N is greater than 1, and detecting one or more artifacts in the acquired data of each revolution. The method further includes the steps of selecting one of the one or more artifacts in each revolution based on predetermined selection criteria and segmenting the data acquired over N revolutions into N-1 data frames each bounded by at least one of the selected artifacts.

In a further aspect of the present invention, a method for artifact management in a rotational imaging system is presented. The method includes the steps of acquiring data employing a helical scanning pattern over N revolutions, where N is greater than 1, and detecting a guidewire shadow artifact in the acquired data of each revolution. The method further includes the steps of segmenting the data acquired over N revolutions into N-1 data frames each bounded by at least one of the guidewire shadow artifacts and normalizing the N-1 data frames into N-1 display frames.

The foregoing and other features and advantages of the invention are defined by the appended claims. The following detailed description of exemplary embodiments, read in conjunction with the accompanying drawings is merely illustrative rather than limiting, the scope being defined by the appended claims and equivalents thereof.

BRIEF DESCRIPTION OF THE DRAWINGS

The foregoing description of the figures is provided for a more complete understanding of the drawings. It should be understood, however, that the embodiments are not limited to the precise arrangements and configurations shown.

The foregoing and other features and advantages of the invention are apparent from the following detailed description of exemplary embodiments, read in conjunction with the accompanying drawings, wherein like structural or functional elements may be designated by like reference numerals.

DETAILED DESCRIPTION OF THE PREFERRED EMBODIMENTS

Language indicative of a relative geometric relationship between components includes use of the terms "proximal" and "distal" herein. In this context, "proximal" refers to an end of a component nearest to the medical practitioner during use and "distal" refers to the end of the component furthest from the medical practitioner during use. FIGS. 4-7 and 9-12B herein are line drawings representative of data acquired by a rotational imaging modality and may be representative of negative images of the actual acquired data. Darker areas in the line drawings represent typically brighter areas as would be displayed, for example, on a video monitor. Likewise, lighter areas in the line drawings represent typically darker areas as would be displayed; thus, a shadow is displayed as white space.

A method for managing artifacts in a rotational imaging system is disclosed herein. The rotational imaging system may be suitable for insertion into a lumen of any anatomical or mechanical conduit, vessel, tube, or the like. The rotational imaging system may comprise an Optical Coherence Tomography ("OCT") system, or may comprise another type of imaging system, including by way of example and not limitation, Intravascular Ultrasound ("IVUS"), spectroscopy, RAMAN, alternative interferometric techniques, therapeutic or diagnostic delivery devices, pressure wires, etc. In the case of an optical imaging system, light sources can be any laser source, broadband source, superluminescent diode, tunable source, and the like. Communication between any proximal and distal end of any of the rotational imaging systems noted hereinabove may be by any communication devices, such as wires, optics, including fiberoptics and/or lens systems, wireless, RF, etc.

Figure 1:
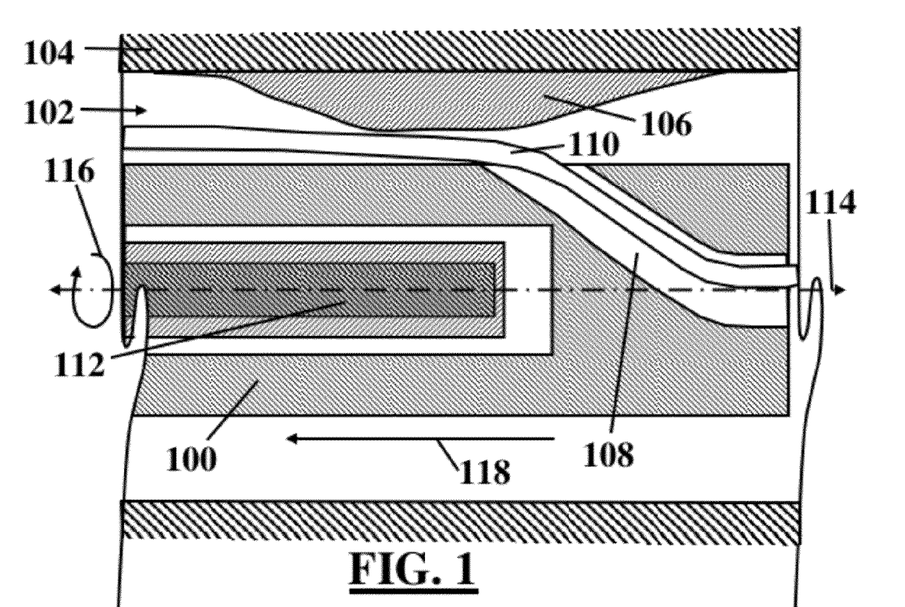
FIG. 1 is a partial cross-sectional view of an imaging catheter suitable for use with a rotational imaging system.

FIG. 1 illustrates an exemplary catheter 100 for rotational imaging inside a lumen of any anatomical or mechanical conduit, vessel, or tube. The exemplary catheter 100 is suitable for in vivo imaging, particularly for imaging of an anatomical lumen or passageway, such as a cardiovascular, neurovascular, gastrointestinal, genitor-urinary tract, or other anatomical luminal structure. For example, FIG. 1 illustrates a vascular lumen 102 within a vessel 104 including a plaque buildup 106. The exemplary catheter 100 may include a rapid access lumen 108 suitable for guiding the catheter 100 over a guidewire 110.

The exemplary catheter 100 is disposed over an exemplary rotational imaging modality 112 that rotates about a longitudinal axis 114 thereof as indicated by arrow 116. The exemplary rotational imaging modality 112 may comprise, in one embodiment, an OCT system. OCT is an optical interferometric technique for imaging subsurface tissue structure with micrometer-scale resolution. In another embodiment, the exemplary rotational imaging modality 112 may comprise an ultrasound imaging modality, such as an IVUS system, either alone or in combination with an OCT imaging system. The OCT system may include a tunable laser or broadband light source or multiple tunable laser sources with corresponding detectors, and may be a spectrometer based OCT system or a Fourier Domain OCT system, as disclosed in U.S. Patent Application Publication No. 2009/0046295, herein incorporated by reference. The exemplary catheter 100 may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both incorporated by reference in their entirety herein.

Figure 2:
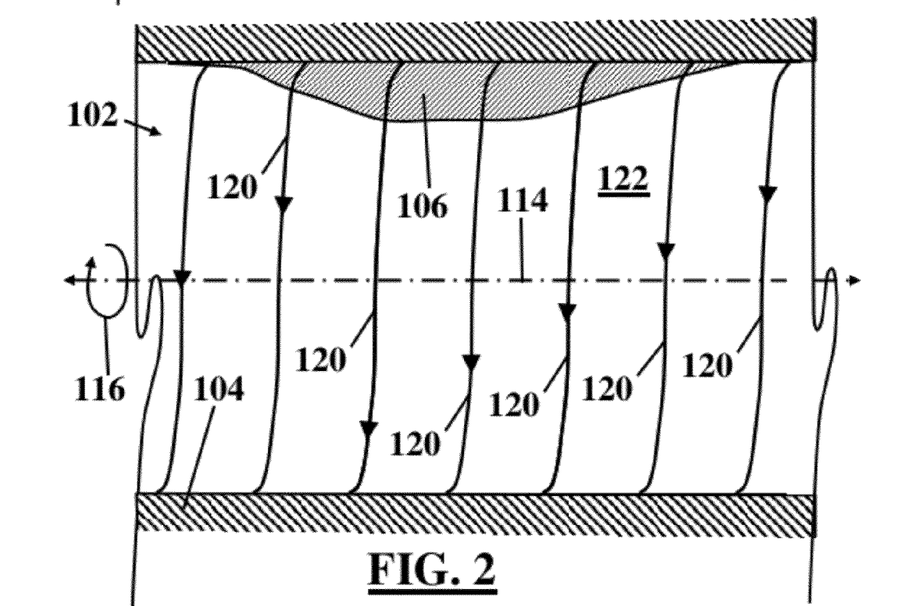
FIG. 2 illustrates a helical scanning pattern for a rotational imaging system.

Referring to FIGS. 1 and 2, the rotational imaging modality 112 may be longitudinally translated during rotation, as indicated by line 118 in FIG. 1. Thus, the rotational imaging modality 112 acquires data along a path 120 that includes a combination of rotation and/or longitudinal translation of the rotational imaging modality 112. FIG. 2 illustrates an exemplary path 120, which is a helical scanning pattern 120, resulting from such a combination. Because FIG. 2 is a cross-sectional view, the helical scanning pattern 120 is illustrated as would be traced on a rear half of a luminal surface 122 of the scanned vessel 104. The helical scanning pattern 120 facilitates scanning a three-dimensional space within and beneath the luminal surface 122 longitudinally as desired, but also introduces a data artifact commonly known as a seam line artifact during reconstruction of the data into a display frame, as will be further discussed hereinbelow.

Referring to FIGS. 1 and 2, the longitudinal axis 114 is illustrated as linear for simplicity and clarity. However, the longitudinal axis 114 is not necessarily linear as illustrated. The longitudinal axis 114 may be curvilinear having a curvature following a tortuosity of the vessel 104. It will be understood that vessel 104 need not be linear, but may in fact have a curvilinear longitudinal axis 104 following the vessel 104 along a tortuous geometry, and that the present invention equally applicable to an imaging modality 112 longitudinally translated along the vessel 104 having a longitudinally linear and/or tortuous geometry.

Figure 3:
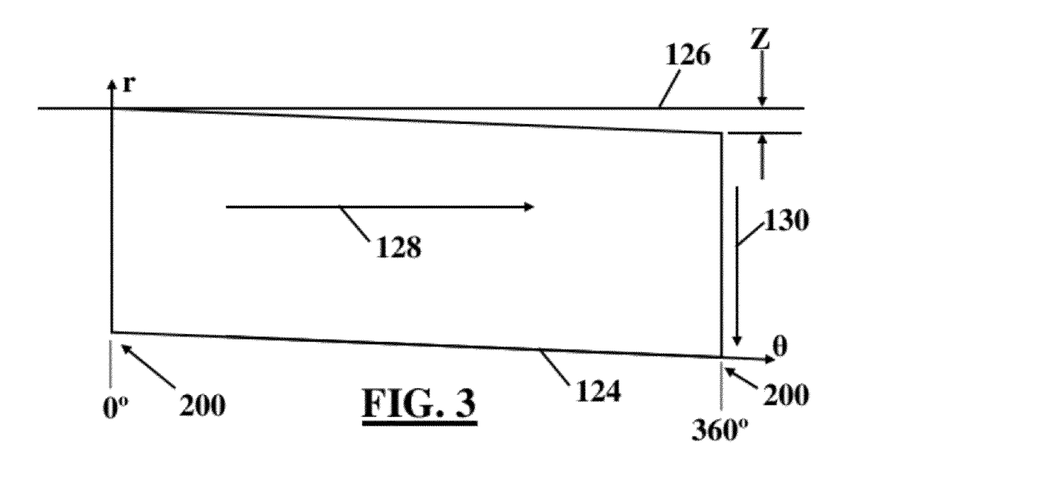
FIG. 3 illustrates the geometry of a data stream acquired using the helical scanning pattern of FIG. 2.

Referring to FIG. 3, a portion of the three dimensional space within and beneath the luminal surface 122 scanned within a single rotational period is projected into a planar (2D) format. In this format, line 126 represents a circumferential axis plotted horizontally. The geometry of a data stream acquired utilizing the above-described helical scan pattern 120 relative to the geometry of the luminal surface 122 may be represented by the parallelogram 124 disposed over the horizontal line 126 in FIG. 3. Starting at a fixed data acquisition angle 200 (hereinafter a "FDAA 200") conveniently denoted as zero degrees (0°) in FIG. 3, the rotational imaging modality 112 acquires data following a rotational path indicated by line 128 (parallel to the line 126) in FIG. 3. However, because the rotational imaging modality 112 may also be translated longitudinally, as indicated by line 130 in FIG. 3, the two-dimensional representation of the scanned three dimensional space within and beneath the luminal surface 122 comprises the shape of the parallelogram 124. This means that at the end of one full rotation of the rotational imaging modality 112 as denoted in FIG. 3 by the FDAA 200 having a value of 360 degrees, the rotational imaging modality 112 has translated longitudinally by a distance Z.

Still referring to FIG. 3, data represented in polar form (r, θ) within the parallelogram 124 includes a radial dimension, r, represented on a vertical axis and a circumferential or angular dimension, θ, represented on the bottom edge of the parallelogram 124. The parallelogram 124 may be thought of as a sequence of thin three-dimensional slices of data taken along FDAA's as the rotational imaging modality 112 rotates within the lumen 120 (See FIGS. 9-11). Thus, the radial dimension, labeled r, represents radial distance from the longitudinal axis 114 (See FIG. 1) so that a smooth circular luminal surface 122 of the vessel 104 would be represented as a straight line parallel to a bottom edge of the parallelogram 124. Fluctuations in radius of the luminal surface 122 would be represented as peaks or valleys varying from the straight line.

Note that the radial dimension r within the acquired rotational period of data as represented by the parallelogram 124 should not be confused with the distance Z that the rotational imaging modality 112 longitudinally translates in one rotation. The radial dimension r applies to the radius of data acquired within each of the three-dimensional slices of data taken along FDAA's, and the distance Z illustrates where that acquired data is acquired longitudinally relative to a fixed point on the lumen 120.

Figure 4:
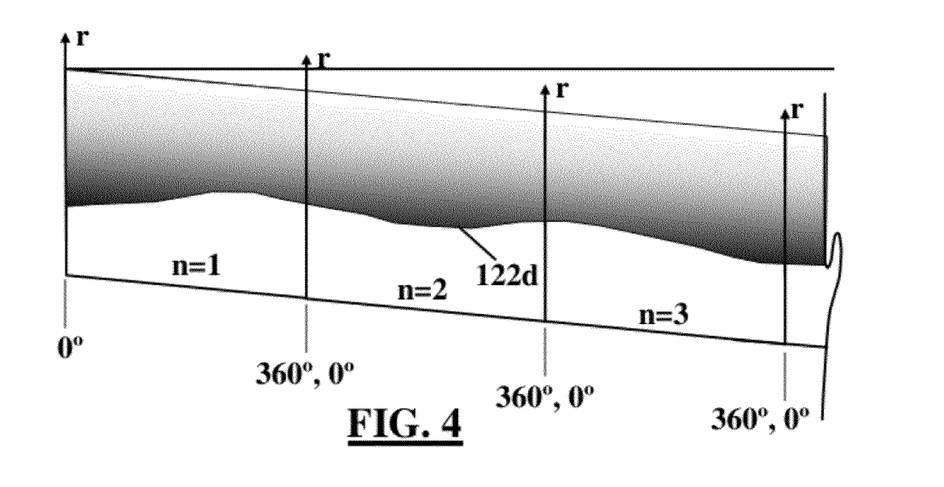
FIG. 4 illustrates an exemplary contour of a vessel surface in the data stream of FIG. 3.

Referring to FIG. 4, a data stream acquired utilizing the above-described helical scan pattern 120 over n rotations of the rotational imaging modality 112 includes, for example, a total of N instances of the luminal surface 122 spanning 360 degrees of rotational arc, where n=1 to N. In this example, the luminal surface 122 is represented by contour line 122d. This form (polar form) of the data facilitates data manipulation and computation; however, a form that shows the actual shape of the luminal surface 122 may be much easier to visualize potential health risks, and therefore may be of much greater use to a medical professional.

Figure 5:
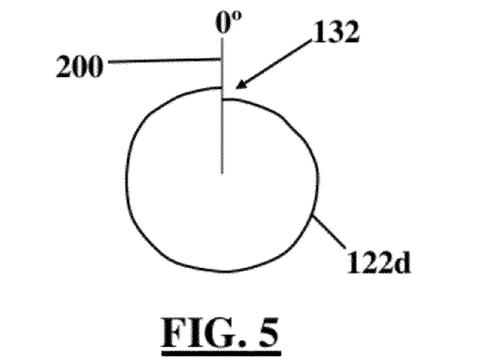
FIG. 5 illustrates a data discontinuity artifact in a display frame due to the helical scanning pattern of FIG. 2.

Referring to FIG. 5, one of the 360 degree instances illustrated in FIG. 4, for example, n=1, has been converted to a display frame for easier visualization. Such conversion between data formats is described in greater detail hereinbelow. FIG. 5 is a simplified line drawing of what an actual display frame would look like and includes the contour line 122d representing the luminal surface 122 of the vessel 104. Although FIG. 5 is a simplified line drawing, an actual display frame (See, e.g., FIGS. 13A-14B) would also include structures beneath the luminal surface 122 that would be displayed as extending outwardly (in a radially increasing direction) away from the contour line 122d. Note that the contour line 122d includes a data discontinuity artifact 132 at a FDAA 200 of zero degrees (0°).

The data discontinuity artifact 132, also referred to as a seam line artifact 132, is a direct result of the helical scanning pattern 120 that results from longitudinal translation of the rotational imaging modality 112 during rotation thereof. This is because a first end of the contour line 122d was acquired by the rotational imaging modality 112 at a first longitudinal position, before translation, and the second end of the contour line 122d was acquired at a second longitudinal position, translated from the first longitudinal position by a distance translated by the rotational imaging modality 112 in one revolution.

Physically, the seam line artifact 132 indicates that the radius of the luminal surface 122 differs for the FDAA 200 of zero degrees between the radius measured before translation and that measured after translation. If, in fact, the radius of the luminal surface 122 were perfectly uniform such that there was no difference between before and after translation, then the contour line 122d in FIG. 5 would be perfectly round lacking a data discontinuity artifact 132. It is often the case that an anatomical lumen does not have a uniform radius. Practically, the seam line artifact is an undesirable nuisance that detracts from visualization of the luminal surface 122 and any underlying structure of interest.

Referring to FIG. 1, the exemplary catheter 100 is typically guided to a treatment/diagnostic site within the vessel 104 by utilization of the guidewire 110. However, the guidewire 110 is a solid elongate object often made of metal and usually opaque to the energy used by the rotational imaging modality 112. Thus, on every rotation the guidewire 110 blocks energy from the rotational imaging modality 112, causing a portion of the retrieved data to be in shadow.

For example, referring to FIG. 6, the exemplary data stream presented hereinabove in FIG. 4 is presented including the effect of a guidewire artifact 202. Because the guidewire 110 casts a shadow 204 outwardly (in a radially increasing direction), a portion of the luminal surface 122 represented by the contour 122d and any features that would otherwise be visible beneath the luminal surface 122 are obscured. The exemplary data stream is presented in polar form and represents multiple periods of rotation of the rotational imaging modality 112 and thus contains multiple periodic instances of the guidewire shadow artifact.

Figure 6:
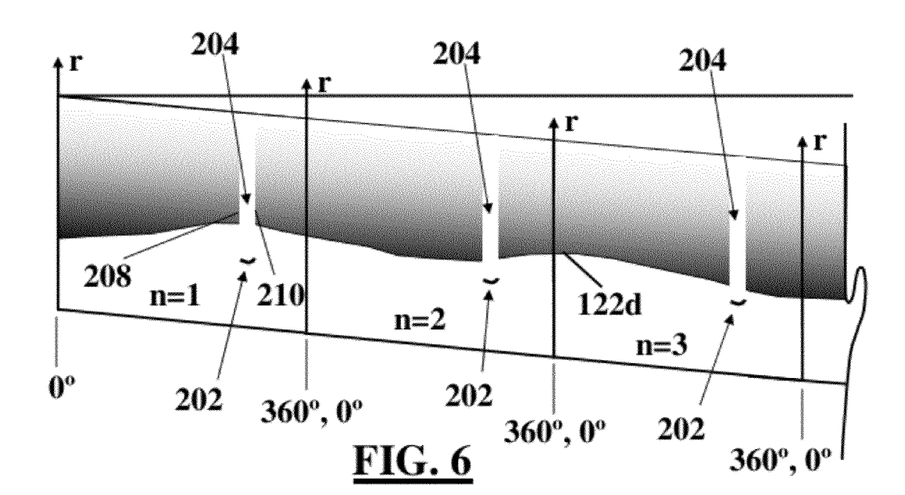
FIG. 6 illustrates a shadow artifact over the exemplary vessel surface contour FIG. 3.
Figure 7:
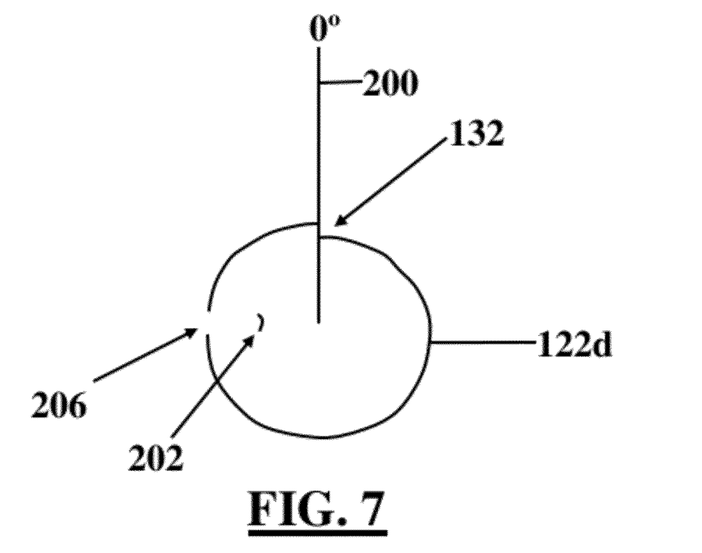
FIG. 7 illustrates the data discontinuity artifact of FIG. 5 and the shadow artifact of FIG. 6 in a display frame.

Referring to FIG. 7, one of the periodic instances illustrated in FIG. 6, for example, n=1, has been converted to a display frame for easier visualization. FIG. 7 is a simplified line drawing of what an actual display frame would look like and includes the contour line 122d representing the luminal surface 122 of the vessel 104. An actual display frame (See, e.g., FIGS. 13A-14B) would also include structures beneath the luminal surface 122 that would be displayed as extending outwardly (in a radially increasing direction) away from the contour line 122d. An actual display frame could further include structures above the luminal surface 122, for example, strut members of a stent that would be displayed within the contour line 122d. In addition to the data discontinuity artifact 132 at a FDAA 200 of zero degrees (0°), the contour line 122d further includes a gap 206 caused by the shadow artifact 204 caused by the guidewire 110, which appears in FIG. 7 as the guidewire artifact 202. As noted hereinabove, the guidewire shadow artifact 204 (and associated gap 206 in reliable imaging data) has traditionally been considered unavoidable but tolerable.

Figure 8:
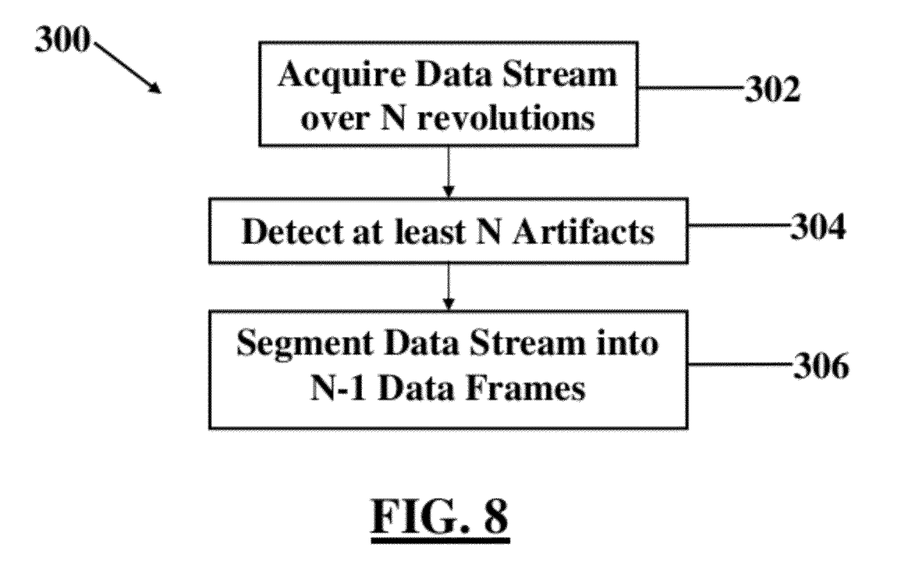
FIG. 8 illustrates an embodiment of a method for managing artifacts in a rotational imaging system.

Referring to FIG. 8, in one embodiment of a method for managing artifacts 300, a data stream is acquired over N revolutions of the rotational imaging modality 112, as described hereinabove and illustrated by Block 302. Next, Block 304 detects at least N artifacts, or at least one artifact for each of N revolutions, as will be described hereinbelow. Following detection, Block 306 segments the data stream comprising N revolutions into N-1 data frames, where each data frame is bounded by the at least one artifact detected in each revolution.

Figure 9:
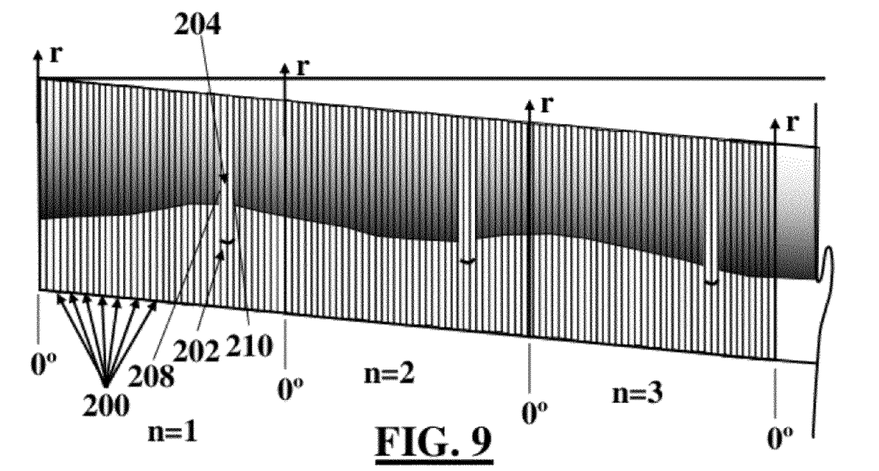
FIG. 9 illustrates data acquisition of the data stream of FIG. 6 via a series of fixed data acquisition angles.

Referring to FIG. 9, the data previously presented in FIG. 6 is presented including exemplary individual FDAA's 200.

In an OCT system, for example, each FDAA 200 would be analogous to an A-scan. The number of FDAA's 200 may vary with rotation speed and acquisition characteristics of a particular rotational imaging modality 112.

Referring to FIGS. 6 and 9, the periodic instances, for example, n=1 to n=3, of the guidewire 202 and the guidewire shadow artifact 204 may be detected using image processing directly on the acquired data, or using a separate synchronization signal acquired via a separate sensor, for example, an alternate optical or acoustic signal. The guidewire artifact 202 and/or shadow artifact 204 may be detected, for example, by utilizing any of several methods described hereinbelow.

Still referring to FIGS. 6 and 9, exemplary methods for detection of a guidewire artifact 202 utilize the fact that because the guidewire 110 is typically made of metal, it produces the guidewire shadow artifact 204. One exemplary method examines each FDAA 200 within a rotation spanning 360 degrees to determine which of the FDAA's 200 includes the guidewire artifact 202 and/or shadow artifact 204. For example, a guidewire artifact 202 may be included in FDAA's 200 having a maximum difference between the brightness of the brightest portion of data in the FDAA 200 and a standard deviation of the brightness in the rest of the FDAA 200. Information useful in implementing this exemplary method may be found, for example, in Kimmel et al. U.S. Pat. No. 7,397,935.

In another exemplary method for detection of a guidewire artifact 202, intensity data in each FDAA 200 is averaged over the entire radial length of the FDAA 200 or over a portion of the radial length of the FDAA 200. A guidewire artifact 202 may be included in FDAA's 200 having a minimum in average intensity or an average intensity that is below a predetermined average value. Information useful in implementing this exemplary method may be found, for example, in Xu U.S. Patent Application Publication No. 2010/0094127.

In yet another exemplary method, a guidewire artifact 202 is associated with those FDAA's 200 in which the intensity profile of acquired data includes a peak intensity above a predetermined peak intensity and a shadow intensity lower than a predetermined shadow intensity. Information useful in implementing this exemplary method may be found, for example, in Unal et al. U.S. Pat. No. 7,801,343.

A further exemplary method for detection of a guidewire artifact 202 utilizes the opaque nature of the guidewire 110 by employing an edge detector as known in the art to detect the guidewire shadow artifact 204 projected by a guidewire 110. In this method, a ridge-detecting filter is applied to the FDAA's 200 to detect edges in intensity, for example, the edges in intensity 208 and 210 of the shadow artifact 204. A ridge intensity map is generated, ridge intensities are radially averaged over each of the FDAA's 200, and features, for example, peaks, valleys, and/or other features in the averaged ridge intensity are associated with the locations of guidewires 110. Information useful in implementing this exemplary method may be found, for example, in Xu U.S. Patent Application Publication No. 2010/0094127.

Figure 10:
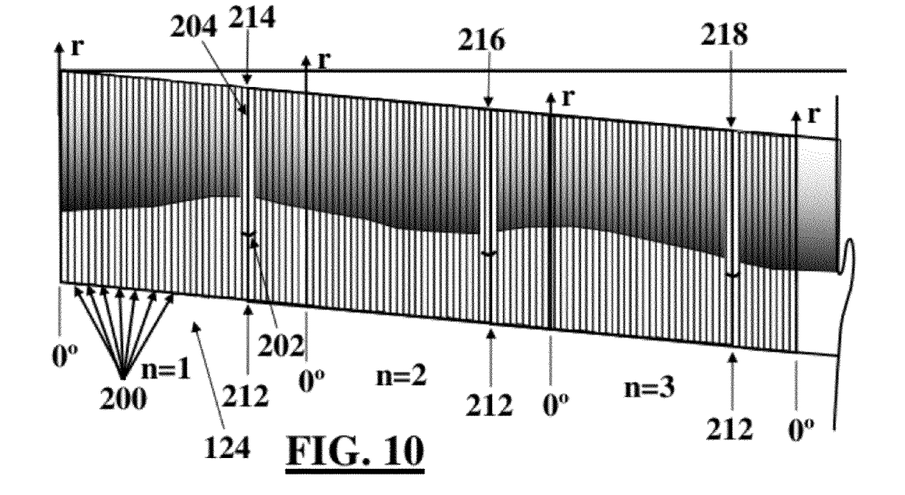
FIG. 10 illustrates artifact detection in the acquired data stream of FIG. 9.

Referring to FIG. 10, one or more of the above-described methods or another method as may be known in the art is utilized to identify or detect the presence of one or more guidewires 110 in each of N rotations of acquired data. Presence of the one or more guidewires 110 is manifested by one or more guidewire artifacts 202 and/or the guidewire shadow artifacts 204 in each rotation. Because the guidewire shadow artifact 204 obscures the vessel wall and any structures of importance therein, the described analysis herein focuses on detection and management of the guidewire shadow artifact 204; however, the analysis is also applicable to detection and management of the guidewire artifact 202.

A rotational position 212 of the FDAA 200 containing each detected guidewire shadow artifact 204 is determined for each rotation, n=1, 2, 3, . . . N. A mathematical identification of the rotational position may be via assignment of an angular value, for example in degrees or radians as a portion of 360 degrees or 2π radians, or as a linear distance measured along the bottom edge of the parallelogram 124. Mathematically, once the rotational positions 212 have been determined, the N revolutions of acquired data may be segmented into N-1 data frames, k=1, 2, 3, . . . N-1, as illustrated in FIG. 11.

In another embodiment, a particular FDAA 200 containing the quidewire artifact 202 and/or the guidewire shadow artifact 204 may be identified in a set of FDAA's 200 spanning one revolution of acquired data. For example, assuming there are about 500 FDAA's 200 spanning the data acquired for one rotation, it may be that the $238^{th}$ such FDAA 200 includes the guidewire artifact 202 and/or the guidewire shadow artifact 204.

Referring to FIG. 10, the guidewire artifact 202 and/or the guidewire shadow artifact 204 may be detected in multiple FDAA's 200 in one or more of the rotations of acquired data. In this case, the above-described methods for detecting which of the FDAA's 200 includes the guidewire 110 are applicable to detect each of the FDAA's 200 that include the guidewire 110 in each rotation. Upon detection of the guidewire artifact 202 and/or guidewire shadow artifact 204, and the assignment of a mathematical position and/or a particular FDAA 200 thereto, the acquired data may be segmented by the Block 306 in FIG. 8.

Figure 11:
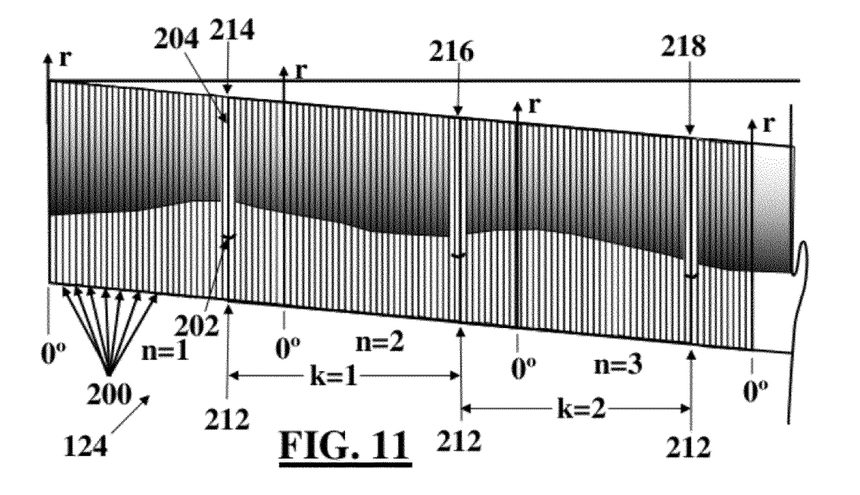
FIG. 11 illustrates segmenting the acquired data stream of FIG. 9.

Referring to FIGS. 10 and 11, one embodiment of a method utilized by the Block 306 for segmenting an acquired data stream of n=1, 2, 3, . . . N revolutions begins by identifying the first instance (in the first rotation n=1) of a guidewire artifact 202 and/or guidewire shadow artifact 204. The n=1 instance of either artifact 202, 204 may be detected in single or multiple FDAA's 200. If the n=1 instance of either artifact 202, 204 is detected in a single FDAA 214, then that particular FDAA 214 is selected as a leftmost FDAA 214 in a K=1 data frame, where K=1, 2, 3, . . . N-1).

If the n=1 instance of either artifact 202, 204 is detected in multiple FDAA's 214, then, in one embodiment, a circumferentially measured center of the n=1 instance of either artifact 202, 204 that is detected in the multiple FDAA's 214 is determined, and segmenting of the acquired data stream is based upon the FDAA 214 that includes the center. For example, if an even number of FDAA's 214 include the n=1 instance of either artifact 202, 204, then the rightmost half of the even number of FDAA's 214 is retained as the leftmost FDAA's of an associated K=1 data frame.

In another embodiment, if the n=1 instance of either artifact 202, 204 is detected in multiple FDAA's 214, then all of the multiple FDAA's 214 that include the n=1 instance of either artifact 202, 204 are retained as the leftmost FDAA's 214 of an associated K=1 data frame. In a further embodiment, if the n=1 instance of either artifact 202, 204 is detected in multiple FDAA's 214, then all of the multiple FDAA's 214 that include the n=1 instance of either artifact 202, 204 are discarded and an associated K=1 data frame is bounded on a leftmost side by an FDAA 214 just to the right of the discarded multiple FDAA's 214.

Referring to FIG. 11, subsequently, a second instance (n=2) of a guidewire artifact 202 and/or guidewire shadow artifact 204 is detected. The n=2 instance of either artifact 202, 204 may be detected in single or multiple FDAA's 200. If the n=2 instance of either artifact 202, 204 is detected in a single FDAA 216, then that particular FDAA 216 is selected as a rightmost FDAA 216 in a K=1 data frame, where K=1, 2, 3, . . . N-1.

If the n=2 instance of either artifact 202, 204 is detected in multiple FDAA's 216, then, in one embodiment, a circumferentially measured center of the n=2 instance of either artifact 202, 204 that is detected in the multiple FDAA's 216 is determined, and segmenting of the acquired data stream is based upon the FDAA 216 that includes the center. For example, if an even number of FDAA's 216 include the n=2 instance of either artifact 202, 204, then the leftmost half of the even number of FDAA's 216 is retained as the rightmost FDAA's of an associated K=1 data frame.

In another embodiment, if the n=2 instance of either artifact 202, 204 is detected in multiple FDAA's 216, then all of the multiple FDAA's 216 that include the n=2 instance of either artifact 202, 204 are discarded and an associated k=2 data frame is bounded on a rightmost side by an FDAA 214 just to the left of the discarded multiple FDAA's 216. In a further embodiment, if the n=2 instance of either artifact 202, 204 is detected in multiple FDAA's 216, then all of the multiple FDAA's 216 that include the n=2 instance of either artifact 202, 204 are retained as the rightmost FDAA's 216 of an associated K=1 data frame.

Following one or more of embodiments of methods for managing artifacts described hereinabove with regard to FIGS. 10 and 11 and applied to segment the acquired data stream into a K=1 data frame, the acquired data is further processed to produce data frames k=2, 3, 4, . . . N-1. Each of the thus segmented data frames can then be scan-converted into Cartesian coordinates for displaying as a display frame in a format representative of true physical space, as described in further detail hereinbelow. The segmented data thus gets displayed, archived, analyzed, etc. similar to segmented data frames that are conventionally segmented, i.e., with a rotational sensor on a drive motor or other rotational timing mechanism.

Figure 12A:
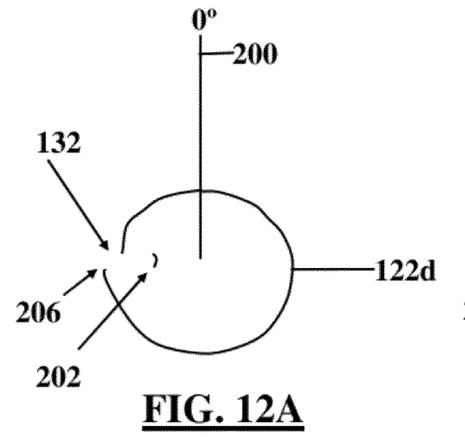
FIG. 12A illustrates a display frame that combines the data discontinuity artifact of FIG. 5 and the guidewire shadow artifact of FIG. 6 into a single artifact.

Once the acquired data has been segmented into properly bounded data frames, a next step may be to normalize the segmented data frames to 360 degrees to create display frames and, if desired, to rotationally register either artifact 202, 204 to the same angle in each of the display frames. For example, in one embodiment, referring to FIG. 12A, a data frame illustrated in FIG. 11, for example, K=1, has been scan-converted to a Cartesian view display frame that shows the actual shape of the luminal surface 122, for example between FDAAs 214 and 216, as the luminal contour 122d. FIG. 12A is a simplified line drawing of what an actual display frame would look like. Note that the acquired data stream segmented as described hereinabove with regard to FIGS. 11 and 12A overlaps the gap 206 caused by the guidewire shadow artifact 204 and the data discontinuity artifact 132. Such overlap provides a better image than an image lacking such overlap for analysis by a medical professional.

Figure 12B:
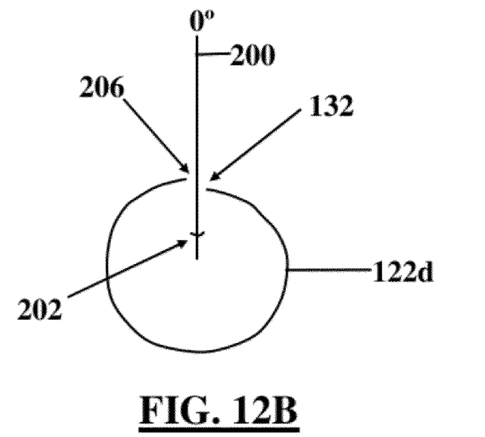
FIG. 12B illustrates a rotationally registered display frame that combines the data discontinuity artifact of FIG. 5 and the guidewire shadow artifact of FIG. 6.

In another embodiment, referring to FIG. 12B, a data frame illustrated in FIG. 11, for example, K=1, has been rotationally registered to a predetermined rotational registration angle following scan conversion to a Cartesian view display frame thus showing the actual shape of the luminal surface 122, for example between FDAAs 214 and 216, as the luminal contour 122d. FIG. 12B is a simplified line drawing of what an actual display frame would look like. Note that the acquired data stream segmented as described hereinabove with regard to FIGS. 11 and 12B overlaps the gap 206 caused by the guidewire shadow artifact 204 and the data discontinuity artifact 132. The overlap has been rotationally registered to occur at a predetermined rotational registration angle, for example at a FDAA 200 of zero degrees (0°). It is preferable that the predetermined rotational registration angle be held constant for all the display frames, K=1, 2, 3, . . . N-1. Such a constant predetermined rotational registration angle or static orientation of the overlap provides a better set of longitudinal cross-sections representing the data (known as the ILD projections) than a set of display frames K=1, 2, 3, . . . N-1 lacking a constant predetermined rotational registration angle for analysis by a medical professional.

Figure 13A:
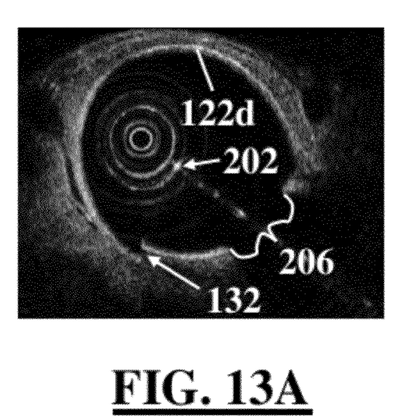
FIG. 13A is an OCT display frame illustrating non-overlapping seam line and guidewire shadow artifacts.

FIG. 13A shows an actual OCT display frame including structure visible beneath the luminal surface 122 displayed in a radially increasing direction away from the contour line 122d. The display frame was generated from acquired data without application of any of the above described methodologies for artifact management. The guidewire artifact 202 and the guidewire shadow artifact 206 are present at about a 4 o'clock position on the image, and the seam line artifact 132 is located at about a 6 o'clock position on the image. The guidewire shadow artifact 206 and the seam line artifact 132 do not overlap, thereby causing the displayed image to include two regions of information discontinuity.

Figure 13B:
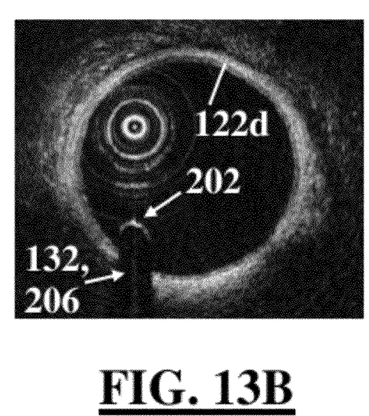
FIG. 13B is an OCT display frame illustrating overlapping seam line and guidewire shadow artifacts.

FIG. 13B shows an actual OCT display frame generated from acquired data via a method for artifact management as described hereinabove. The guidewire artifact 202, the guidewire shadow artifact 206, and the seam line artifact 132 are co-located at about a 6 o'clock position on the image. Such co-location produces a single gap in the information acquired and provides an improved image appearance for an end user of the image.

Figure 14A:
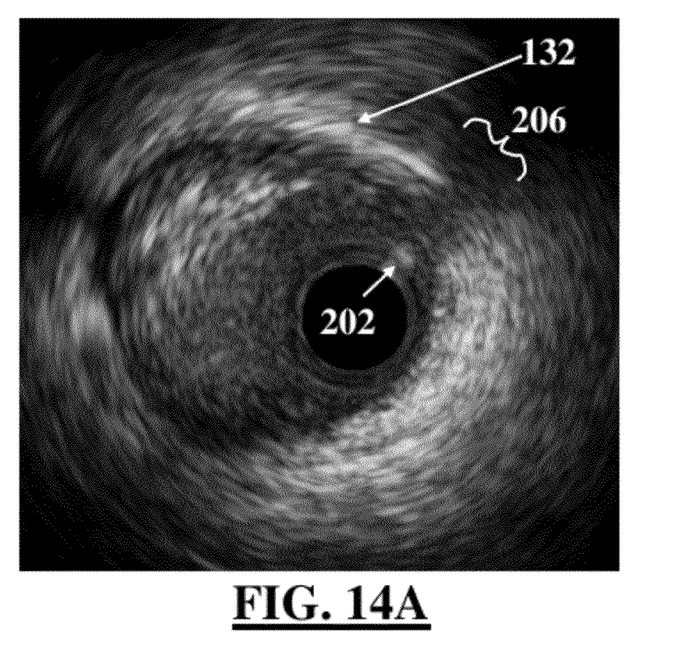
FIG. 14A is an IVUS display frame illustrating non-overlapping seam line and guidewire shadow artifacts.

FIG. 14A shows an actual IVUS display frame generated from acquired data without application of any of the above described methodologies for artifact management. The guidewire artifact 202 and the guidewire shadow artifact 206 are present at about a 2 o'clock position on the image, and the seam line artifact 132 is located at about a 12 o'clock position on the image. The guidewire shadow artifact 206 and the seam line artifact 132 do not overlap, thereby causing the displayed image to include two regions of information discontinuity.

Figure 14B:
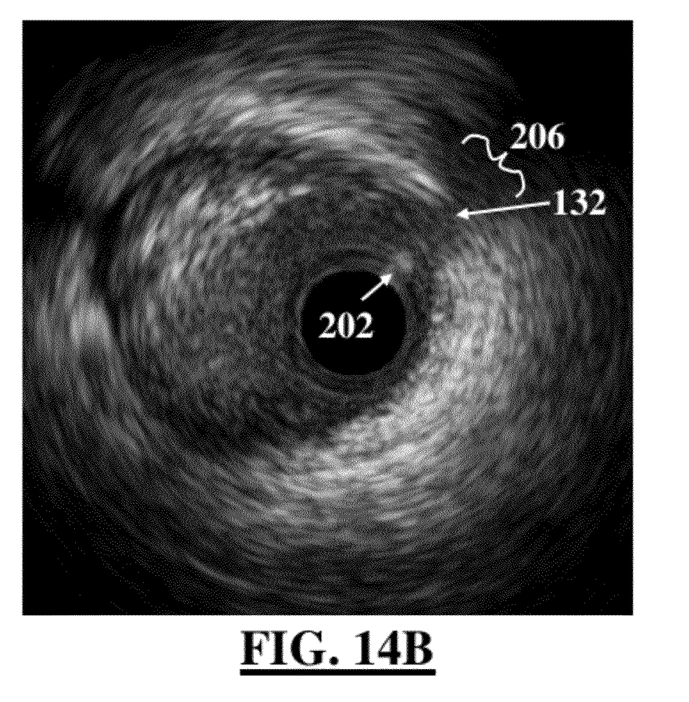
FIG. 14B is an IVUS display frame illustrating overlapping seam line and guidewire shadow artifacts.

FIG. 14B shows an actual IVUS display frame generated from acquired data via a method for artifact management as described hereinabove. The guidewire artifact 202, the guidewire shadow artifact 206, and the seam line artifact 132 are co-located at about a 2 o'clock position on the image. Such co-location produces a single gap in the information acquired and provides an improved image appearance for an end user of the image.

Multiple guidewires 110 can be present in the vessel lumen 102. In such an instance, the multiple guidewires 110 would generate multiple guidewire shadow artifacts 204. The methods described hereinabove for detection and segmentation of a guidewire shadow artifact 204 are applicable to detect and segment multiple such artifacts 204 per revolution of the rotational imaging modality 112. For example, in one embodiment, in a first step, a plurality of detected artifacts 204 is identified in the acquired data for the $k^{th}$ revolution, where K=1, 2, 3, . . . N-1. Next, a plurality of detected artifacts 204 is identified in the acquired data for the $k+1^{st}$ revolution. Each of the plurality of detected artifacts in the acquired data for the $k^{th}$ revolution is matched with each of the plurality of detected artifacts in the acquired data for the $k+1^{st}$ revolution. Subsequently, the one of the plurality of detected artifacts 204 in the acquired data for the $k^{th}$ revolution that comprises the largest number of acquired adjacent FDAA's 200 is selected for segmentation and the process verifies that that the one of the plurality of detected artifacts 204 in the acquired data for the $k+1^{st}$ revolution matching the selected one of the plurality of detected artifacts 204 in the acquired data for the $k^{th}$ revolution comprises the largest number of acquired adjacent FDAA's 200 of any of the plurality of detected artifacts 204 in the acquired data for the $k+1^{st}$ revolution.

Figure 15:
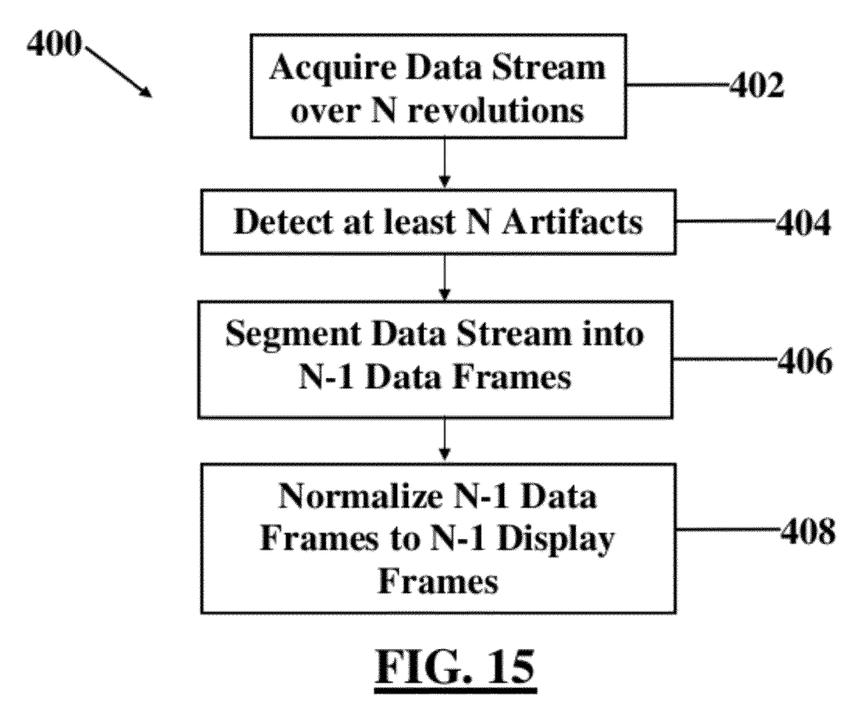
FIG. 15 illustrates another embodiment of a method for managing artifacts in a rotational imaging system.

The number of FDAA's (e.g. A-scans) between guidewire shadow artifacts 204 in the acquired data stream may not necessarily be constant. Therefore, referring to FIG. 13, in another embodiment 400 of a method for managing artifacts in a rotational imaging modality 112, a normalization process is included in addition to the Blocks 302, 304, and 306 of the method 300 described hereinabove with regard to FIG. 8. Block 408 executes the normalization process to normalize each display frame to a frame representative of an entire rotation (360°) of the rotational imaging modality 112.

For example, in one embodiment, the Block 408 computes the number of FDAA's 200 that would be present in a full rotation of data acquisition based upon the speed of rotation and the speed of data acquisition of the rotational imaging modality 112. The Block 408 determines a correction factor based on the difference in actual FDAA's 200 present in a display frame as determined by one or more of the methods described hereinabove, and the computed number of FDAA's. The Block 408 applies the correction factor to the data to scan-convert the acquired data in polar form to display frames in Cartesian form.

In another exemplary embodiment, the Block 408 standardizes each display frame to have a uniform number of FDAA's 200. The Block 408 in this embodiment may increase or decrease the number of FDAA's per display frame to some constant value. Subsequently, the Block 408 operates on the constant number of FDAA's by, for example, interpolating, sub-sampling, and/or duplicating/borrowing lines from neighboring display frames to produce a display frame representative of an entire rotation (360°) of the rotational imaging modality 112.

A method for detection and management of imaging artifacts in data acquired using any rotational imaging modality is presented. The method minimizes the effects of both the seam line and guidewire shadow artifacts by orienting the seam line artifact so that it overlaps the guidewire artifact in a Cartesian image. The method advantageously reduces two discontinuous image artifacts in a display frame (the seam line and guidewire shadow) into a common rotational position, which results in a single traditionally tolerable gap in the information acquired and improved image appearance for an end user of the image.

It will be appreciated by those skilled in the art that changes could be made to the embodiments described hereinabove without departing from the broad concepts disclosed therein. Accordingly, the systems and methods of use described herein may be embodied in many different forms and should not be construed as limited to the embodiments set forth herein. The systems and methods of use described herein may take the form of an entirely hardware embodiment, an entirely software embodiment, or an embodiment combining software and hardware aspects. The systems and methods of use described herein can be performed using any type of computing device, such as a computer, that includes a processor or any combination of computing devices where each device performs at least part of the process or method.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

It will be understood that each Block of the FIGS., and combinations of Blocks in the FIGS., as well any portion of the systems and methods disclosed herein, can be implemented by computer program instructions. These program instructions may be provided to a processor to produce a machine, such that the instructions, which execute on the processor, create means for implementing the actions specified in the Block or Blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the method for artifact management in rotational imaging described herein and to teach the best mode of carrying out the same.

We claim:

1. A method for artifact management in an intravascular rotational imaging system, the method comprising the steps of:
   acquiring rotational image data from a rotating probe of an intravascular rotational imaging system, wherein each frame of the image data comprises a seam line artifact and a guidewire shadow artifact;
   transmitting the data to a computing device that comprises a processor;
   processing on the computing device the data to produce an intravascular image wherein the seam line artifact overlaps with the guidewire artifact in the image; and
   displaying the processed image.

2. The method according to claim 1, wherein the image data is acquired employing a helical scanning pattern over N revolutions, where N is greater than 1.

3. The method according to claim 2, wherein processing comprises:
   detecting at least one artifact in the acquired data of each revolution; and
   segmenting the data acquired over N revolutions into N-1 data frames each bounded by at least one of the at least one artifacts.

4. The method of claim 3, wherein the step of detecting further includes the steps of:
   generating a ridge intensity level map from the acquired data;
   averaging the ridge intensity level along a fixed data acquisition angle for all the fixed data acquisition angles in the acquired data; identifying features in the average ridge intensity level for the acquired data; and
   associating at least one feature in the average ridge intensity level in the acquired data of each revolution with the at least one artifact.

5. The method of claim 3, wherein the step of detecting further includes the steps of:
   following a path through the acquired data along increasing radius for a fixed data acquisition angle;
   measuring an intensity profile along the path; incrementing the fixed data acquisition angle to an adjacent fixed data acquisition angle; and
   repeating the following and measuring and incrementing steps until the intensity profile along the path of the last fixed data acquisition angle is measured.

6. The method of claim 5, wherein the step of detecting further includes the following steps after the incrementing step:
   determining the fixed data acquisition angles for which the intensity profile includes a peak intensity above a predetermined peak intensity and a shadow intensity lower than a predetermined shadow intensity.

7. The method of claim 5, wherein the step of detecting further includes the following steps after the incrementing step:
   determining the fixed data acquisition angles for which an average of the intensity profile averaged along the path is below a predetermined average.

8. The method of claim 5, wherein the step of detecting further includes the following steps after the incrementing step:
   determining the fixed data acquisition angles for which a difference between a maximum intensity of the path and the standard deviation of the path excluding the maximum intensity is above a predetermined difference.

9. The method of claim 3, wherein the step of segmenting further includes the step of normalizing the N-1 data frames into N-1 display frames each spanning 360 degrees.

10. The method of claim 9, further including a step of rotationally registering each of the at least one of the at least one artifacts to a constant predetermined rotational registration angle for each of the N-1 display frames each spanning 360 degrees.

* * * * *